(12) United States Patent
Lacombe et al.

(10) Patent No.: US 7,950,801 B2
(45) Date of Patent: May 31, 2011

(54) DEVICE AND METHOD FOR MEASURING THE CONTRAST OF THE FRINGES IN A MICHELSON INTERFEROMETER AND SYSTEM FOR EXAMINATION OF THE EYE COMPRISING SUCH A DEVICE

(75) Inventors: François Lacombe, Chaville (FR); David Lafaille, Meudon (FR)

(73) Assignees: Centre National de la Recherche Scientifique, Paris (FR); Observatoire de Paris, Paris (FR); Mauna Kea Technologies, Paris (FR)

( * ) Notice: Subject to any disclaimer, the term of this patent is extended or adjusted under 35 U.S.C. 154(b) by 680 days.

(21) Appl. No.: 10/586,897

(22) PCT Filed: Jan. 21, 2005

(86) PCT No.: PCT/FR2005/000135
§ 371 (c)(1),
(2), (4) Date: Jul. 21, 2006

(87) PCT Pub. No.: WO2005/080912
PCT Pub. Date: Sep. 1, 2005

(65) Prior Publication Data
US 2008/0225231 A1    Sep. 18, 2008

(30) Foreign Application Priority Data
Jan. 22, 2004  (FR) ..................... 04 00580

(51) Int. Cl.
*A61B 3/10*   (2006.01)
*A61B 3/14*   (2006.01)

(52) U.S. Cl. ........ 351/206; 351/209; 351/210; 351/211; 351/215

(58) Field of Classification Search ............ 351/211, 351/205; 930/60; 365/230.03; 530/307
See application file for complete search history.

(56) References Cited

U.S. PATENT DOCUMENTS

| 3,849,001 A | 11/1974 | Inoue et al. |
| 4,076,423 A * | 2/1978 | Bates ............ 356/364 |
| 4,541,697 A | 9/1985 | Remijan |

(Continued)

FOREIGN PATENT DOCUMENTS

WO    WO 03/020121    3/2003

(Continued)

OTHER PUBLICATIONS

C.K. Hitzenberger, et al.; Differential Phase Contrast in Optical Coherent Tomography; Optics Letters; vol. 24, No. 9, May 1, 1999, pp. 622-624, XP001183361; p. 622-623.

*Primary Examiner* — Ricky L Mack
*Assistant Examiner* — Mahidere S Sahle
(74) *Attorney, Agent, or Firm* — Greer, Burns & Crain, Ltd.

(57) ABSTRACT

The invention relates to a device, for measuring the contrast of fringes in a Michelson interferometer at full field, comprising a Wollaston prism for diverting two perpendicular incident polarizations into two different emergent directions, said diverting means being arranged within the interferometer as substitute for a single polarizer. The device is of application to a Michelson interferometer used in an OCT tomographical system and comprising means for obtaining interferometric contrast without use of a modulation technique or synchronous detection methods.

24 Claims, 3 Drawing Sheets

U.S. PATENT DOCUMENTS

| | | | |
|---|---|---|---|
| 4,938,584 A * | 7/1990 | Suematsu et al. | 351/211 |
| 5,239,411 A | 8/1993 | Espie et al. | |
| 5,877,856 A * | 3/1999 | Fercher | 356/492 |
| 5,883,692 A * | 3/1999 | Agonis et al. | 351/224 |
| 5,973,784 A | 10/1999 | Szwaykowski et al. | |
| 5,975,699 A * | 11/1999 | Hellmuth | 351/211 |
| 6,588,900 B1 | 7/2003 | Le Gargasson et al. | |
| 2003/0218755 A1 * | 11/2003 | Wei et al. | 356/497 |
| 2004/0189941 A1 | 9/2004 | Bucourt et al. | |

FOREIGN PATENT DOCUMENTS

| | | |
|---|---|---|
| WO | WO 03/105678 A2 | 12/2003 |
| WO | WO 03/105678 A3 | 12/2003 |

* cited by examiner

DEVICE AND METHOD FOR MEASURING THE CONTRAST OF THE FRINGES IN A MICHELSON INTERFEROMETER AND SYSTEM FOR EXAMINATION OF THE EYE COMPRISING SUCH A DEVICE

This invention relates to a device for measuring the contrast of fringes in a Michelson interferometer operating in full-field mode. It also relates to a method implemented in this device, as well as a system for examination of the eye comprising such a device.

Figure 1:
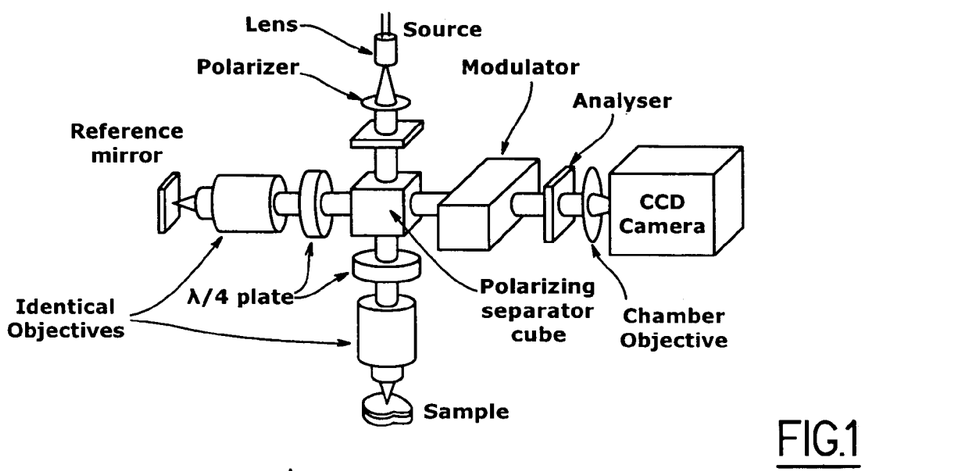
FIG. 1 is a block diagram of a full-field OCT tomography system representative of the prior art.

Full-field Michelson interferometry is an interferometric technique derived from the conventional Michelson set up which makes it possible, inter alia, to deduce the surface profiles and reflectance of a sample from the interferences produced between the light reflected by the sample and that originating from a reference arm. When it is used with a light source that is temporally of low coherence, this technique has a tomographic capacity in media that are transparent and weakly diffusing. This is called full-field optical coherence tomography (OCT). FIG. 1 thus illustrates the structure of an OCT tomography system by full-field interferometry representative of the prior art.

For the study of media that are possibly birefringent, on the one hand, but also with the desire to collect the maximum amount of light returning from the sample, full-field OCT has often been used in polarized light. In this case, the two arms of the Michelson interferometer operate with perpendicular polarizations. The interferences are produced on the output arm only after projection on a common axis by using a 45 degree analyser.

Interferometric modulation, hitherto necessary for the detection of interferences of low amplitude, is produced either by moving the mobile mirror of the reference arm, or by modulating the optical path of one of the polarizations on the output arm of the interferometer, for example, by using a photo-elastic modulator before the 45 degree analysis. Interferogram amplitude measurements under mediocre signal/noise conditions ratio often lead to the consideration of techniques for modulating the difference in interferometric path coupled with synchronous detection techniques.

The phase state of the interferograms obtained will be modified temporally so as to be able to eliminate any possibly variable continuous component of the measured signal, which results from the incoherent combination of the output signals, due either to parasitic reflections, or to reflections with path differences greater than the coherence length of the radiation used.

When mechanical stability, thus interferometric, of the entire system imposes high modulation frequencies, it happens that the detection chain, most frequently a CCD sensor in the full-field case, cannot operate properly. In general, this becomes the factor limiting the modulation/detection frequency and thus the ability of the system to observe fringes.

During the analysis of a Michelson interferogram, at least three interferogram measurements at different phase states are necessary in order to deduce without ambiguity the amplitude and phase of the interferogram. For practical reasons, most frequently the option is for four independent measurements for sequence differences separated by a quarter of a wavelength. There are thus four measurements that must be taken in the characteristic time where the system of interferences can be considered as stable. This requirement makes the implementation of a synchronous detection even more difficult.

When the temporal stability of the interferogram is defective, or the detection sequence cannot achieve the required frequencies, measurement becomes difficult or even impossible.

At the output from a Michelson interferometer, a 45 degree polarizer of the incident polarization directions is normally used, the direction of which the fields originating from the two arms of the interferometer are projected onto. Interferences then become apparent. On this projection, half the incoming energy is lost, which contributes to a downgrading of the performances of the interferometer.

The purpose of this invention is to remedy this drawback by proposing a device to measure the contrast of the fringes in a Michelson interferometer, making it possible to simultaneously obtain interferograms in different phase states, which provides access to a measurement of their amplitude and even of their phase, despite potential instabilities. This invention is applied to the case of full field interferograms in polarized light.

This objective is achieved with a contrast measuring device comprising means to deflect two incoming perpendicular polarizations in two different emerging directions, these deflection means being arranged within the interferometer as a substitution for the single polarizer.

The lost light is the projection of the fields onto a direction perpendicular to the direction of the polarizer. However, on this direction, interferences could also be observed. Replacing the single polarizer by a Wollaston prism enables the two outputs to be used as the outputs of two perpendicular polarizers which would be used simultaneously. The whole of the incoming light is thus used.

The deflection means may advantageously be provided in the form of a Wollaston prism, the axes of which are orientated at 45 degrees to the polarizations of the arms. This prism is a common commercial device which is commonly used to angularly separate radiations that are linearly polarized. The angle of separation is a characteristic of the Wollaston prism and can be chosen from a wide range.

Installing a Wollaston prism at the output of a full-field Michelson interferometer thus makes it possible to produce several simultaneous interferograms at different phase states. It makes the extraction of amplitude and phase data from the radiations originating from the interferometer particularly simple and robust. The device according to the invention is applied particularly well in the case of tomography by full-field OCT on samples that are mechanically unstable at an interferometric scale.

When the Michelson interferometer is implemented in an OCT tomography system, extraction of the interferometric contrast of the data is carried out, given the very low value of this contrast, by using modulation techniques associated with synchronous detection methods. Two to four measurements, depending on the case, obtained for path differences differing by $\lambda/2$ or $\lambda/4$ as appropriate, are thus taken. These measurements are, by the same modulation principle, obtained on different dates. To guarantee the coherence of these measurements dictates a capability to guarantee the invariance of the constant path difference (not including the desired modulation). At $\lambda=780$ nm, for a sampling frequency of 100 Hz, for example, to guarantee the path difference to within $\lambda/4$, is expressed by imposing a variation of the path difference less than $V=100*\lambda/4=2$ µm/sec. Such a constraint makes any measurement in vivo almost impossible.

A second objective of this invention is to resolve this problem relating to the variability of the path difference. This objective is achieved with the use of a Wollaston prism, which makes it possible to obtain at least two measurements that are strictly simultaneous and in phase opposition. In fact, if the first projection leads to the quantity:

$$Ia = I1 + I2 + 2 \cdot \sqrt{(I1 \cdot I2)} \cdot \cos(\phi) \qquad (I)$$

where φ is the phase shift between the two channels, then the second projection leads to:

$$Ia = I1 + I2 - 2 \cdot \sqrt{(I1 \cdot I2)} \cdot \cos(\phi) \qquad (II)$$

Which is also written:

$$Ib = I1 + I2 + 2 \cdot \sqrt{(I1 \cdot I2)} \cdot \cos(\phi + \pi) \qquad (III)$$

We therefore have simultaneously two embodiments of the interference system with two path differences separated by λ/2.

Another problem encountered in a Michelson interferometer relates to the availability of four measurements by modulation. In fact, obtaining four measurements poses even more problems than obtaining two measurements by modulation, still for reasons of variability of the path difference.

This problem of availability of four measurements is resolved by separating the beam into two parts using a single non-polarizing separating plate. In one of the two beams produced, an additional delay of λ/4 is imposed between the polarizations originating from the two arms of the interferometer. A quarter-wave plate can impose this delay. The two beams thus processed are then reintroduced together and with a small angle, into the Wollaston prism such that, on leaving the latter, there are then four beams with the following intensities:

$$Ia = I1 + I2 + 2 \cdot \sqrt{(I1 \cdot I2)} \cdot \cos(\phi) \qquad (IV)$$

$$Ia = I1 + I2 + 2 \cdot \sqrt{(I1 \cdot I2)} \cdot \cos(\phi + \pi/2)$$

$$Ia = I1 + I2 + 2 \cdot \sqrt{(I1 \cdot I2)} \cdot \cos(\phi + \pi)$$

$$Ia = I1 + I2 + 2 \cdot \sqrt{(I1 \cdot I2)} \cdot \cos(\phi + 3\pi/2)$$

The interferograms must be consistent, i.e. the phase shift imposed (0, π/2, π, 3π/2) must be constant in the field.

To this end, the Wollaston prism is used in a pupil plane. All points of the field thus see the same portion of the prism, which guarantees the fixed condition of constant phase shift in the field.

It should be noted that the equations (IV) mentioned above are only valid if the angle of direction of the polarizations is rigorously equal to 45 degrees. In order to achieve this objective, there is a half-wave plate preceding the Wollaston prism. This half-wave plate can orient arbitrarily, but together, the polarizations of the four incident beams relative to the Wollaston prism's own axes. The Wollaston prism is thus precisely aligned relative to the detector, for example, according to the direction of separation parallel to the lines of the detector, without any assumption on the precise alignment of the incident polarizations relative to it. The half-wave plate plays an interface role between the set up upstream of the Wollaston prism and the set up downstream.

The desired modulation frequencies are generally fairly high, which imposes fairly short exposure and reading times. This problem of image rate and exposure time is resolved with a simultaneity of measurements which thus eliminates any need for speed for the detector. The briefness of the exposure, if appropriate, can be ensured by the briefness of the lighting, for example a flash, without the integration of the detector, or its reading, being brief or rapid.

According to another aspect of the invention, a system for examining the eye by in vivo tomography is proposed, comprising:

a Michelson interferometer, producing a full-field OCT set up, adaptive optical means, arranged between the interferometer and an eye to be examined, producing a correction of the wavefronts originating from the eye as well as those reaching the eye, and means of detection, arranged downstream of the interferometer, making it possible, without synchronous modulation or detection, to carry out the interferometric measurement according to the OCT principle, characterized in that it also comprises a device for measuring the contrast of the fringes in a full-field Michelson interferometer, this device comprising means of deflecting two incoming perpendicular polarizations in two different emerging directions.

This examination system according to the invention may also advantageously comprise a sighting device comprising at least one moving target having a programmable shape and trajectory, this at least one target being displayed on an appropriate screen, visible by both eyes, during the examination period.

Other advantages and characteristics of the invention will become on examination of the detailed description of one embodiment, which is in no way limitative, and the attached figures, in which.

Figure 2:
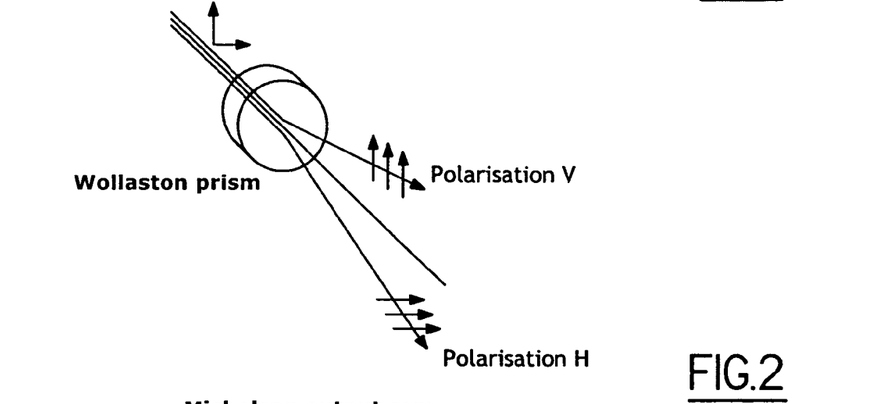
FIG. 2 illustrates the principle of a Wollaston prism implemented in an improvement device according to the invention.
Figure 3:
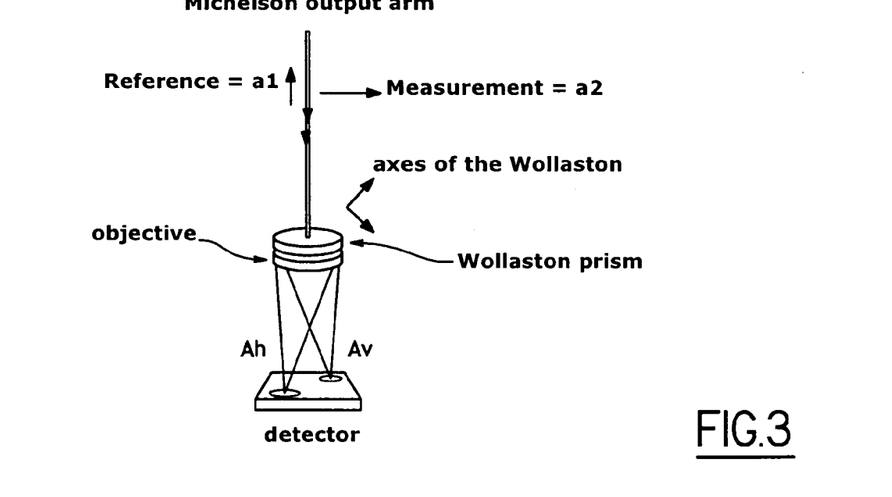
FIG. 3 illustrates diagrammatically a first configuration, for the measurement in two phases, of a contrast improvement device according to the invention.

Firstly, the principle of measurement in two phases used in the device according to the invention will now be described with reference to FIGS. 2 and 3.

If $a_1$ (or respectively $a_2$) is called the amplitude of the electric field originating from the reference (or respectively measurement) arm of the Michelson interferometer, the projection on one of the axes of the Wollaston prism has an amplitude:

$$Av = \sqrt{2}/2(a_1 + a_2)$$

whereas the projection on the other axis of the Wollaston prism will have an amplitude:

$$Ah = \sqrt{2}/2(a_1 - a_2)$$

The two projections are separated angularly by the characteristic angle of the Wollaston prism. Focussed by the objective of the chamber, they produce two juxtaposed interferometric images of the field, in which the energies are expressed as:

$$Iv = |Av|^2 \text{ and } Ih = |Ah|^2$$

i.e.

$$Iv = \tfrac{1}{2}(a_1^2 + a_2^2 + 2a_1 \cdot a_2 \cdot \cos(\phi))$$

and $$Ih = \tfrac{1}{2}(a_1^2 + a_2^2 - 2a_1 \cdot a_2 \cdot \cos(\phi))$$

where $\phi$ is the phase shift between the two radiations $a_1$ and $a_2$.

The second equality can also be written:

$$Ih = \tfrac{1}{2}(a_1^2 + a_2^2 + 2a_1 \cdot a_2 \cdot \cos(\phi+\pi))$$

Thus, we obtain simultaneously two images corresponding to two states of the interferogram in phase opposition. The duration of the exposure (or of the illumination of the sample) can be made arbitrarily short, within the detection limit, in order to guarantee the "freezing" of the interferometric information. Nevertheless, the simultaneity of the two measurements and hence the phase shift of $\pi$, is never questioned. It should also be noted that this phase shift is obtained mathematically, by construction, and is totally achromatic.

In reality, the quantity $a_2$ must be viewed as the superposition of a radiation of amplitude $a_{2_0}$ which does not interfere with $a_1$ unless a path difference is sufficiently small, and a radiation of amplitude $a_{2*}$ reflected with a path difference less than the coherence length of the source used which itself does interfere. We therefore have:

$$Iv = \tfrac{1}{2}(a_1^2 + a_2^2 + 2a_1 \cdot a_{2*} \cdot \cos(\phi))$$

$$Ih = \tfrac{1}{2}(a_1^2 + a_2^2 + 2a_1 \cdot a_{2*} \cdot \cos(\phi+\pi))$$

The quantity actually modulated is derived from the difference between Ih and Iv:

$$Im = 2a_1 \cdot a_{2*} \cdot \cos(\phi)$$

This is the same quantity as that obtained by synchronous detection, but therefore at the cost of a temporal dichotomy of the measurement, as half the interrogation time must be devoted to each measurement, at $\phi$ and $\phi+\pi$.

In addition to simultaneity, this method therefore offers a photometric advantage which has its origin in the fact that the two possible projections at 45 degrees are processed. All the available energy is used. However, the quantity Im does not separate $a_{2*}$ from $\phi$, by considering $a_1$ as known. There is still an ambiguity between the amplitude and the cosine of the phase.

Figure 4:
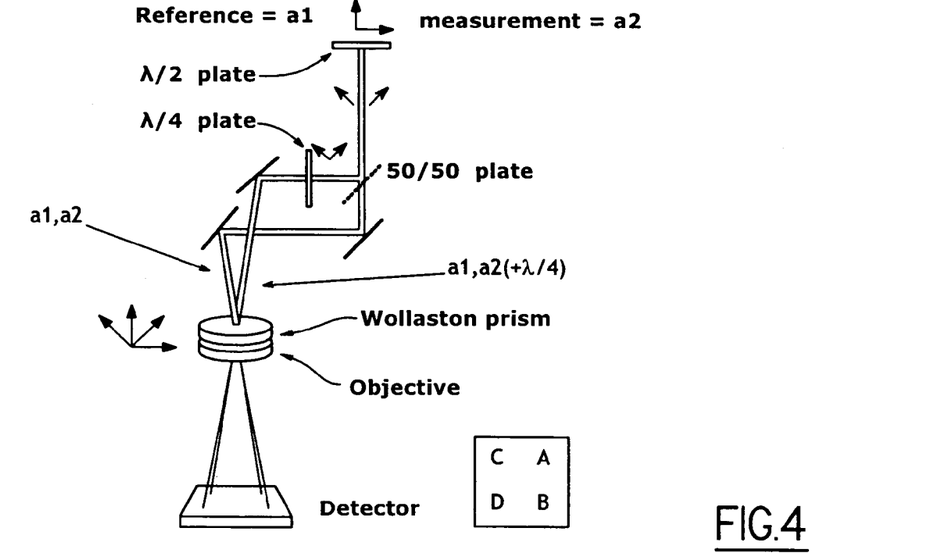
FIG. 4 illustrates diagrammatically a second configuration, for the measurement in four phases, of a contrast improvement device according to the invention.

In a second configuration of the device according to the invention illustrated by the FIG. 4, a measurement is carried out according to four phases. Using a semi-reflecting plate, 50% of the energy is sampled before the Wollaston prism. On the deflected beam, where the radiations from the two arms which are still polarized perpendicularly are found, a quarter-wave plate is installed, in which the axes are aligned with the two incident polarizations. An additional phase shift of $\pi/2$ is therefore imposed between the two arms.

It is then sufficient to inject the beam into the same Wollaston prism, but with a small angle relative to the undeflected beam, which can also be chosen equal to the characteristic angle of the Wollaston prism, in order to obtain four beams separated angularly at the output. For practical reasons, the assembly may be preceded by a half-wave plate the function of which is to prepare the orientation of all the polarizations.

The amplitudes of the field in the four beams are:

$$A_A = \tfrac{1}{2}(a_1 + a_2)$$

$$A_B = \tfrac{1}{2}(a_1 - a_2)$$

$$A_C = \tfrac{1}{2}(a_1 + a_2[\pi/2])$$

$$A_D = \tfrac{1}{2}(a_1 - a_2[\pi/2])$$

where $a_2[\pi/2]$ represents the amplitude of the radiation $a_2$, phase shifted by $\pi/2$.

Four measured intensities correspond to these four amplitudes:

$$I_A = \tfrac{1}{4}(a_1^2 + a_2^2 + 2a_1 \cdot a_2 \cdot \cos(\phi))$$

$$I_B = \tfrac{1}{4}(a_1^2 + a_2^2 - 2a_1 \cdot a_2 \cdot \cos(\phi))$$

$$I_C = \tfrac{1}{4}(a_1^2 + a_2^2 + 2a_1 \cdot a_2 \cdot \cos(\phi+\pi/2))$$

$$I_D = \tfrac{1}{4}(a_1^2 + a_2^2 - 2a_1 \cdot a_2 \cdot \cos(\phi+\pi/2))$$

or again:

$$I_A = \tfrac{1}{4}(a_1^2 + a_2^2 + 2a_1 \cdot a_{2*} \cdot \cos(\phi))$$

$$I_B = \tfrac{1}{4}(a_1^2 + a_2^2 - 2a_1 \cdot a_{2*} \cdot \cos(\phi))$$

$$I_C = \tfrac{1}{4}(a_1^2 + a_2^2 + 2a_1 \cdot a_{2*} \cdot \cos(\phi+\pi/2))$$

$$I_D = \tfrac{1}{4}(a_1^2 + a_2^2 - 2a_1 \cdot a_{2*} \cdot \cos(\phi+\pi/2))$$

This time, there are indeed four simultaneous interferometric images of the field, corresponding to four different phase states of the interferogram, from which the two quantities are derived in a conventional manner:

$$Im_1 = I_A - I_B = a_1 \cdot a_{2*} \cdot \cos(\phi)$$

$$Im_2 = I_C - I_D = a_1 \cdot a_{2*} \cdot \cos(\phi+\pi/2) = a_1 \cdot a_{2*} \cdot \sin(\phi)$$

Which enables the phase to be eliminated by sum of the squares:

$$I = Im_1^2 + Im_2^2 = a_1^2 \cdot a_{2*}^2 = I_1 \cdot I_{2*}$$

where $I_1$ and $I_{2*}$ are the intensities returned by the reference arm of the Michelson interferometer and the sample, at the depth selected by the length of the reference arm. From the ratio of $Im_1$ and $Im_2$, $tg(\phi)$ can be derived independently of $I_{2*}$.

If the use of the Wollaston prism gives access to simultaneous measurements of the interferogram in different phase states, these measurements are nevertheless taken with detectors or pixels from different CCD sensors. A careful calibration of the individual sensitivity and the bias for each pixel must therefore be carried out in order to eliminate any bias in the calculation of the differences $Im_1$ and $Im_2$ and thus the sum of their squares.

A practical example of an in vivo tomography system according to the invention will now be described with reference to FIG. 5, incorporating an interferometric contrast measurement device. This system comprises a full-field interferometer of the Michelson type, comprising a measurement arm provided to illuminate the eye and collect the returned light, and a reference arm provided to illuminate a moving mirror enabling in depth exploration of the retinal tissue.

The interferometer is used with light polarized rectilinearly and perpendicularly in the two arms. The light source S is a diode with a short temporal coherence length (for example, 12 μm), the spectrum of which is centred on 780 nm. In theory, it confers on the in vivo tomography an axial resolution equal to half the coherence length divided by the refractive index of the medium.

This light source S can be pulsed. In this case, it is then synchronised with the shot of the image and the adaptive correction. The beam is limited by a field diaphragm corresponding to 1 degree in the field of view of the eye (300 μm on the retina) and a pupil diaphragm corresponding to an opening of 7 mm on a dilated eye.

An input polarizer P provides optimal balancing of the flux injected into the two arms of the interferometer.

The two arms have a configuration termed Gauss, afocal, which enables the conjugation of the pupils on the one hand, and the materialisation of an intermediate image of the field where a diaphragm blocks a large part of the corneal reflection, on the other hand. Quarter-wave plates ensure by the rotation of polarization of the sole light returned by the eye, and the moving mirror, an effective filtering of parasitic reflections in the in vivo tomography system according to the invention.

In order to maintain the equality of the optical paths in the two arms, with the same conjugation of the pupils and of the field, the reference arm is similar to the measurement arm but with a static optic.

The detection path of the in vivo tomography system according to the invention will now be described. The two beams on the output arm are still polarized perpendicularly, and they interfere only if they are projected in a common direction. A Wollaston W prism has the function of simultaneously projecting the two radiations in two perpendicular analysis directions. A simultaneous measurement of the intensity can then be made after interference in two interference states in opposition, without synchronous modulation or detection, on a single two-dimensional detector. The addition of a quarter-wave plate, after division of the beam, enables to access two additional measurements, thus removing any ambiguity between the amplitude and phase of the fringes. A half-wave plate at the input to the detection path enables suitable orientation of the incident polarizations.

The Wollaston prism is arranged in a pupil plane, hence conjugated with the separator cube of the Michelson interferometer. The separation angle of the Wollaston prism is chosen as a function of the field to be observed. The focal length of the final objective determines the sampling interval of the four images.

The detector is of the CCD type, with an image rate of more than 30 images per second. This detector is associated with a dedicated computer (not shown) in which the digital processing of the images is carried out: extraction of the four measurements, calibration, calculation of the amplitude of the fringes.

The adaptive correction of the wavefronts is carried out upstream of the interferometer and thus in the measurement arm. Each point of the source S thus sees its image on the retina corrected of aberrations, and the return image is also corrected. The amplitude of the fringes is thus maximum.

The adaptive optics sub-assembly comprises a deformable mirror MD. Measurement of the wavefront is carried out by an analyser SH of the Shack-Hartmann type on the return beam of a luminous spot itself imaged on the retina via the deformable mirror MD. The analysis wavelength is 820 nm. Illumination is continuous and provided by a temporally incoherent superluminescent diode SLD. The dimensioning of the analyser corresponds to an optimisation between photometric sensitivity and wavefront sampling. The control refreshment frequency of the deformable mirror MD can reach 150 Hz. A dedicated computer (not shown) manages the adaptive optical loop. The control is, however, synchronised in order to freeze the shape of the mirror during the interferometer measurement.

An appropriate check on the focussing of the analysis path, using a lens LA2, enables to adapt the focussing distance to the layer selected by the interferometer. This arrangement is essential for maintaining an optimum contrast at any depth.

The deformable mirror MD is conjugated with the pupil of the system and of the eye. The field of the system is defined by the system input field diaphragm DCM. It is chosen to be a value of 1 degree, thus less than that of the isoplanetism field of the eye, which guarantees the validity of the adaptive correction in the field of the only wave front measurement made from the spot, at the centre of the field. Moreover, the rotation of the deformable mirror MD makes it possible to choose the angle of arrival of the beam in the eye and thus the portion of the retina studied.

The OCT measurement assumes the equality of the optical paths between the two arms of the Michelson interferometer, to within the coherence length of the source. It also assumes an optimum adjustment on the depth which corresponds to this equality. Conventionally, the limitation on the diameter of the beam confers on the eye a very large depth of field, which dispenses with any readjustment.

When the system is used at full opening (typically F/3), the field depth reduces rapidly, typically 30 μm. The Z scanning of the OCT can produce a rapid exit from this interval, above which the interferometric contrast reduces. This can be considered as an aberration effect of pure defocus.

This problem can be remedied by providing the wave surface analyser with a device capable of adjusting its own focussing, for example with a mechanical adjustment. An arbitrary modification of this focussing forces, via the adaptive optical loop, the deformable mirror to adopt an additional curvature, conjugating input source and detector with a point more or less deep in the retina. The control of this focussing should be synchronized with the Z scanning of the OCT.

It is also possible to control the analyser in order to force it to work in an unfocussed mode. Some advanced analysers, for example models from the company Imagine Optic, are actually capable of working in unfocussed mode with good results.

An alternative solution to an actual defocussing of the analyser may consist of adding a pure focus term into the mirror control, regardless of the analyser measurement. This artifice is commonly used in adaptive optics. With an analyser of the Shack-Hartmann type, one just has to modify the table termed "reference slopes" which forces the system to converge towards an arbitrarily modified control.

The addition of corrective lenses to the subject's view, thus of low orders of geometric aberrations such as focus or astigmatism, just in front of the eye, makes it possible to drop the requirements on the travel of the deformable mirror MD, and also guarantees an improved sighting. An adaptive corrective system by transmission may be used in preference to static lenses for an optimum correction.

A sighting device according to the invention, collaborative or active, is installed upstream of the assembly. This sighting system, which comprises an active target pattern MAM, presents to the subject the image of a luminous point, deviating periodically from the sought sighting axis. The patient is then invited to follow all the movements of this image. Each time that the image returns to the axis, and after an adjustable latency time, a series of interferometric measurements is carried out. The periodic movement of the view makes it possible to obtain from the patient an improved fixation capacity when he aims at the desired axis. The amplitude and the frequency are adaptable to the subject and to the measurements undertaken. For reasons of convenience, the target pattern can be produced with a simple office computer on which a luminous point is displayed and moved. The active target pattern MAM, the adaptive optics, the source S and the image shot are synchronized.

Figure 5:
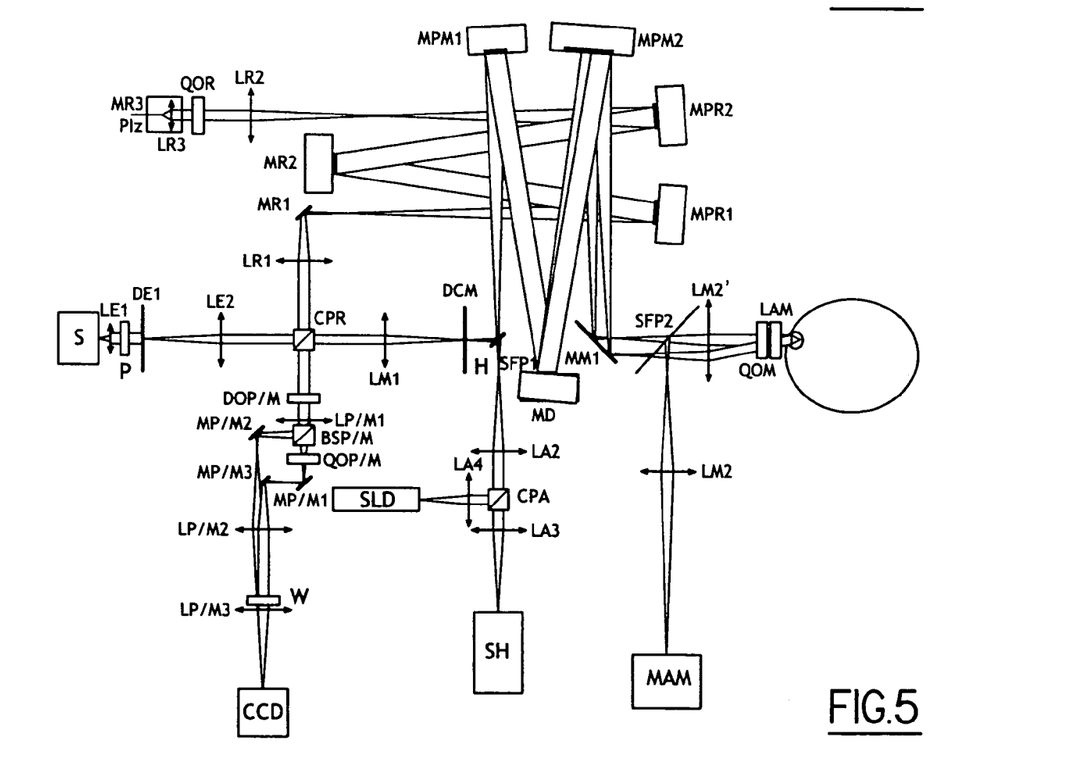
FIG. 5 illustrates diagrammatically a practical example of the embodiment of an in vivo tomography system integrating a contrast improvement device according to the invention.
Figure 6:
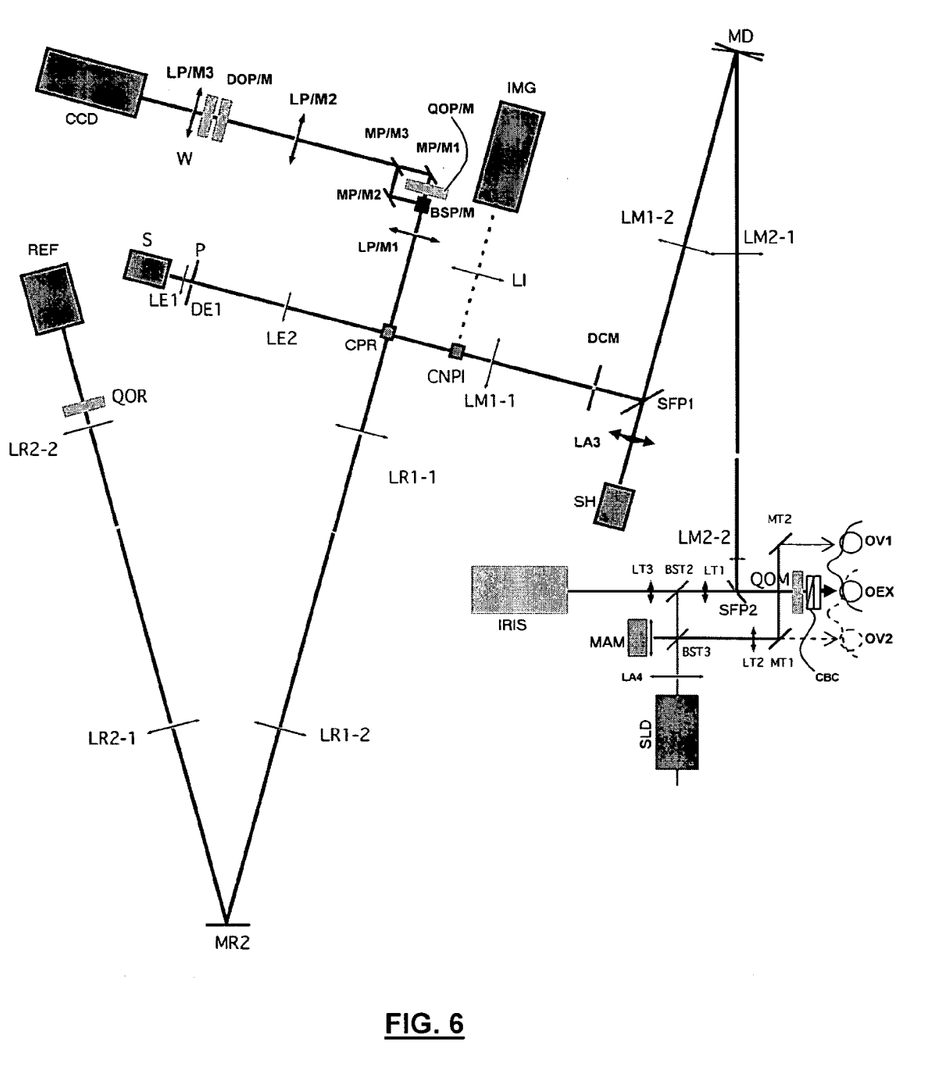
FIG. 6 is a diagram of another embodiment of an in vivo tomography system according to the invention.

In the practical embodiment illustrated by FIG. 5, the in vivo tomography system according to the invention is relatively compact at less than 1.2 m sideways. A significant part of the size constraint comes from the diameter of the deformable mirror MD which fixes in part the focal length of the off-axis parabolas. The use of micro-mirrors would obviously reduce all the dimensions of the system.

The detection system, with its division into two beams, is produced here with discrete components. The production and use of integrated components combining the functions of separation, folding or even delaying the beams may be envisaged.

As regards analysis of the wavefront, it will be noted that the installation of the reference source SLD upstream of the deformable mirror MD enables optimum quality of aberration measurements and thus their compensation, as the reference image materialised in the eye benefits in this case from adaptive correction. This optimisation remains true whatever the focussing, the source SLD being upstream of the adjustment control system. Finally, the use of a polarizing cube CPA (FIG. 4) here makes it possible to use all the photons originating from the eye. Measurement of the wavefront is therefore made under good conditions.

However, it should be noted that a very precise lateral optical conjugation is required between the reference source SLD and the input of the analyser SH. If this conjugation is insufficient, an attempt at compensation by the adaptive optical loop can lead to a divergence of the servo-control.

A variant of the invention, illustrated in FIG. 5, allows greater simplicity in the system, by reducing this risk of instability in the adaptive optical loop. In this variant, the reference source SLD is positioned closer to the eye in the optical path, in particular after the adaptive optics (outwards) and, for example, before a birefringence compensator, such as a Soleil-Babinet compensator CBC, or just before the eye. In the absence of benefiting from an optimum image spot at the base of the eye, the system then benefits from operational stability.

The deformable mirror used in the adaptive optics may be, for example, a 50 mm diameter mirror with 31 elements from the CILAS company. However, the performances and/or compactness of the device may be improved by using a higher performance and/or more compact model such as the deformable 15 mm diameter mirror with 52 elements developed at the Astrophysics Laboratory of the Grenoble Observatory, in particular due to its compactness and a larger travel in the adaptation movements.

In the example illustrated in FIG. 5, the folding reflectors of the measurement arms MPM1, MPM2 and those of the reference arms MPR1, MPR2 have been eliminated. The optical path of the measurement arm comprises a doublet of two lenses LM1-1 and LM2-2 on one side of the deformable mirror MD, and another doublet of two lenses LM2-1 and LM2-2 on the other side of this deformable mirror. Similarly, the optical path of the reference arm comprises a doublet of two lenses LR1-1 and LR2-2 on one side of the reference mirror MR, and another doublet of two lenses LR2-1 and LR2-2 on the other side of this reference mirror.

The use of lenses rather than mirrors can be more economical and allow better performance, in particular due to the cost and the optical aberrations of this type of mirror, which are typically off-axis parabolic mirrors.

The combination of such an on axis set up, with a smaller deformable mirror, make it possible to obtain a system which performs better, is simpler, or is more economic, while retaining a limited size.

As illustrated in FIG. 5, the system can also comprise conventional imaging means, such as a camera IMG, capable of combining interferometric measurements with a simple imaging of the zones examined, for example to facilitate the exploration and selection of the zones to be examined.

Arranged directly at the output (on the return way) of the measurement arm, and therefore just in front of the polarizing cube CPR of the interferometer, a second polarizing cube CNPI may deflect the return beam to an imaging camera IMG having its own means LI of focussing the image. On this path, a direct image of the sighted retinal zone will be observable. In particular the measurement arm and this additional path may be arranged such that a wider field of observation is provided than with the interferometric mode, the field of which is limited, in particular by the interferometric contrast measurement technique in itself.

Due to its low coherence length, the input source S has a spectrum of the polychromatic type. In a typical OCT set up, this spectrum is in general relatively narrow, for example with a width of approximately 50 nanometers, but not necessarily negligible.

This polychromatic spectrum can cause a deterioration in performance, in particular by leading to a dispersion of the path differences due to the dispersive characteristics of the ocular environment, which leads to a deterioration in the axial resolution of the device. In order to avoid or limit these deteriorations, the system may comprise compensation means situated in the reference arm.

Moreover, the dispersive character of ocular media is also manifested by a variation in the focus of the eye with the wavelength, also leading to a deterioration in axial resolution. In order to avoid or limit these deteriorations, the system may therefore comprise compensation means situated for example in the measurement arm. In particular, these means may compensate for a focal chromatism which represents approximately 400 micrometers between the red and the blue, for example by replacing the collimator LM2-2 situated just in front of the eye by a doublet with chromatism chosen deliberately opposite to that of the eye. These means may also compensate for optical path differences due to chromatic dispersion, for example by inserting a water tank into the reference arm of a size dependent and/or controllable according to the size or to the characteristics of the eye to be examined. Such a tank may have a size of the order of 24 mm, the average length of a human eye.

With a 12 micrometers coherence length source and spectrum width of 50 nanometers, the use of these compensation means may enable improvement in the axial resolution by changing it from a value of approximately 6 micrometers to a value of approximately 4 micrometers. In order to improve performance, in particular in terms of axial resolution, the system may also use as input source for the interferometer a polychromatic illumination with a wider spectrum, for example white light. In this case, the improvement in performance provided by these compensating means will be much more significant.

The invention may in particular be used to produce or complement a device for retinal imaging, or for corneal topography, or for measuring a film of tears.

Of course, the invention is not limited to the examples which have just been described and numerous adjustments can be made to these examples without exceeding the framework of the invention.

The invention claimed is:

1. A device for measuring the contrast of fringes in a full-field Michelson interferometer having at least means for separating a source beam into one reference arm and one measurement arm, the reference arm and the measurement arm co-operating with an output arm, which receives a reference signal and a measurement signal from the separating means, in order to produce an optical coherence tomography (OCT) system, said device comprising:

means for deflecting two incoming signals issued from the reference arm and the measurement arm of the Michelson interferometer having perpendicular polarizations in at least two different emerging directions and a beam detector, said means for deflecting being arranged between the means for separating and said beam detector within the output arm of the full-field Michelson interferometer said means for deflecting (W) being oriented so that at least two interferometric images of an observed point are formed through an interference of projection of the reference signal and the measurement signal on an axis of said means for deflecting and respectively an interference of projection of the reference signal and the measurement signal on another axis of said means for deflecting (W).

2. The device according to claim 1, wherein the means for deflection comprise a Wollaston prism.

3. The device according to claim 2, wherein it is arranged to carry out measurements for path differences differing by λ/2 or λ/4.

4. The device according to claim 3, wherein it is arranged to obtain at least two measurements, strictly simultaneous and in phase opposition.

5. The device according to claim 2, wherein it is arranged to carry out four measurements, and further means for separating a beam comprising a reference signal and a measurement signal, entering into the detection output arm into at least two separate sub-beams, means of generating, in one of said two sub-beams, an additional delay of λ/4 between the polarizations originating from the measurement arm and the reference arm of the interferometer, and means for reintroducing together the two beams thus processed into the Wollaston prism such that, on output from the latter, there are then four light beams forming four interferometric images of the field.

6. The device according to claim 1, wherein the separator means comprise a single non-polarizing separator plate.

7. The device according to claim 5, wherein the delaying means comprise a quarter-wave plate.

8. The device according to claim 5, wherein the Wollaston prism is arranged in a pupil plane.

9. The device according to claim 5, wherein it also comprises means for arbitrarily orienting the polarizations of four incident beams relative to the Wollaston prism's own axes.

10. The device according to claim 9, wherein the means for orienting comprise a half-wave plate preceding the Wollaston prism.

11. A method for measuring the contrast of fringes in a full-field Michelson interferometer including at least one reference arm and one measurement arm co-operating with an output arm, which receives a reference signal and a measurement signal from a means for separating a source beam, to produce an optical coherence tomography system, the method comprising the steps of:

introducing a reference beam and a measurement beam into the output arm from a further beam splitter and deflecting two incoming beams issued from the reference arm and the measurement arm of the Michelson interferometer having perpendicular polarizations in at least two different emerging directions producing at least two interferometric images by means of a Wollaston prism situated between said beam splitter and a beam detector in said output arm of the full-field Michelson interferometer through an interference of projection of said reference beam and said measurement beam on an axis of the Wollaston prism and respectively an interference of projection of said reference beam and said measurement beam on another axis of the Wollaston prism.

12. The method according to claim 11, further including measurements for path differences differing by λ/2 or λ/4.

13. The method according to claim 12, further including at least two measurements, strictly simultaneous and in phase opposition.

14. The method according to claim 11, further including four measurements, a separation into two sub-beams of a beam comprising a reference signal and a measurement signal entering the output arm, a generation, in one of the two separated sub-beams produced, of an additional delay of λ/4 between the polarizations originating from the measurement arm and the reference arm of the interferometer, and a reintroduction of the two sub-beams thus processed into the Wollaston prism such that, on output from the latter, there are then four light beams forming four interferometric images of the field.

15. The method according to claim 14, further including an arbitrary orientation of the polarizations of the four incident beams relative to the Wollaston prism's own axes.

16. The method according to claim 15, wherein the measurements on the four beams are carried out simultaneously.

17. The method according to claim 11, further including, in the measurement arm, a compensation for the effects of focal chromatism of the eye.

18. The method according to claim 11, further including, in the reference arm, means for compensating for the dispersion of the path differences.

19. The method according to claim 11, further including a control of a wave front analyzer obliging it to work in defocused mode.

20. A system for examining the eye by in vivo tomography, comprising:

a Michelson interferometer, comprising at least means for separating a source beam into one measurement arm and one reference arm co-operating with an output arm which receives a reference beam and a measurement beam from said means for separating in order to produce a full-field OCT setup, adaptive optical means, arranged between the measurement arm of the interferometer and an eye to be examined or within said measurement arm, carrying out the correction of the wavefronts originating from the eye as well as those reaching the eye, means of detection, arranged downstream of the interferometer or within its output arm, making it possible to carry out the interferometric measurement according to the optical coherence tomography (OCT) principle, and a device for measuring the contrast of fringes in a full-field Michelson interferometer, said device comprising in the output arm, means for deflecting two incoming signals issued from said reference arm and said measurement arm of the Michelson interferometer polarizations in at least two different emerging directions, said means for deflecting being positioned between said means for separating and said means of detection in said output arm, said means for deflecting being oriented so that at least two interferometric images of an observed point are formed through an interference of projection of said reference signal and said measurement signal on an axis of said means for deflecting and respectively an interference of projection of said reference signal and said measurement signal on another axis of said means for deflecting.

21. The system for examining the eye according to claim 20, further including a sighting device comprising at least one moving target having a programmable shape and trajectory, said target being displayed on an appropriate screen, visible by both eyes, during the examination period.

22. The system according to claim 20, wherein the reference source is inserted into the optical path between the adaptive optical means and the eye to be examined.

23. The system according to claim 20, further including, in the measurement arm, means for compensating for the effects of focal chromatism of the eye.

24. The system according to claim 20, further including, in the reference arm, means for compensating for the dispersion of the path differences.

* * * * *